US00PP32717P2

(12) United States Plant Patent
Olesen

(10) Patent No.: US PP32,717 P2
(45) Date of Patent: Jan. 5, 2021

(54) MINIATURE ROSE PLANT NAMED 'POULPAH096'

(50) Latin Name: *Rosa hybrida*
Varietal Denomination: Poulpah096

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,260

(22) Filed: Sep. 3, 2019

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./116, 123

CPC ..... A01H 5/02; A01H 5/0222; A01H 5/00; A01H 6/749; A01H 6/74
See application file for complete search history.

(56) References Cited

PUBLICATIONS

Floral Daily Nordic Flower Expo 2015, retrieved on Mar. 3. Jan. 2020, retrieved from the Internet at https://www.floraldaily.com/photos/album/9055/nordic-flower-expo-2015/, cover page and p. 106. (Year: 2015).*
Nolina Growers with Passion Catalog 2015, retrieved on Mar. 31, 2020, retrieved from the Internet at https://www.nolina.nl/image/redactoruploadfile/Nolina_Brochure_Finished%20plants.pdf, cover page, pp. 02,03,05. (Year: 2015).*
Poulsen Roser A/S Noriko, retrieved on Apr. 1, 2020, retrieved from the Internet at http://www.poulsenroser.com/assortment/rose-collections/patiohit/fiorella-hit.aspx, 2 pp. (Year: 2020).*

* cited by examiner

*Primary Examiner* — June Hwu

(57) ABSTRACT

A new garden rose plant of the miniature class which has abundant, pink and white striped flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah096'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpah096', originated as a single seedling from the stated cross.

The new variety may be distinguished from its male pollen parent and female seed parent primarily by the following characteristics. The male pollen parent plant has ivory white flowers while the new variety has pink and white striped flowers. The female seed parent plant has solid pink flowers while the new variety has pink and white striped flowers.

The objective of the hybridization of this rose variety was to create a new and distinct variety with unique qualities, such as:

1. Uniform and abundant pink and white striped flowers;
2. Vigorous, but compact growth when propagated on its own roots;
3. Exceptional disease resistance.

This combination of qualities is not present in previously available commercial cultivars of this type, known to the inventor, and distinguish 'Poulpah096' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpah096' was selected in the spring of 2013 by the inventor as a single plant from the progeny of the aforementioned hybridization.

Asexual reproduction of 'Poulpah096' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpah096' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah096'.

Specifically illustrated in FIG. 1 of the drawings are open flowers with petals detached revealing the receptacle and peduncle, detached sepals, and juvenile trifoliate leaf.

Figure 1:
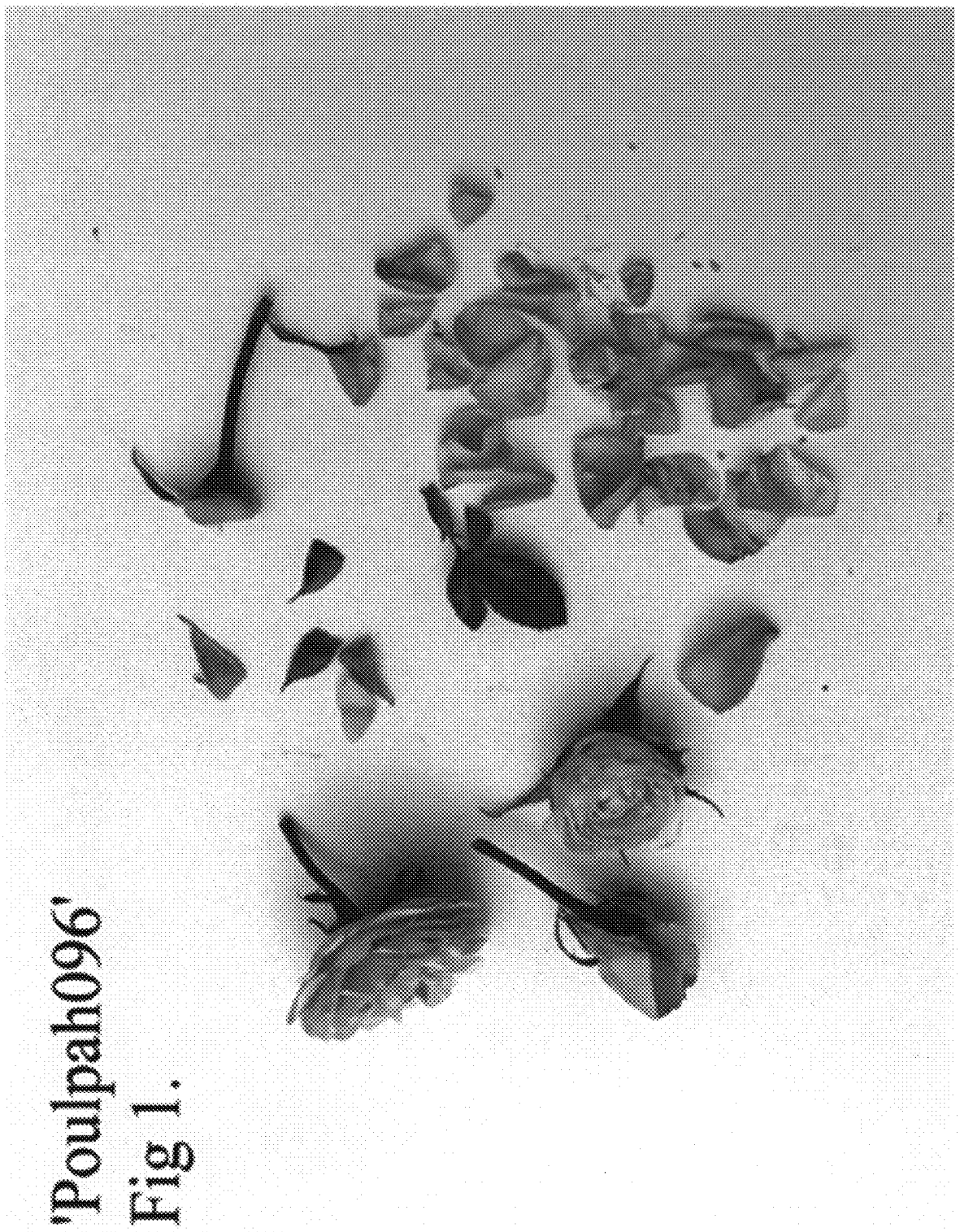
Figure 2:
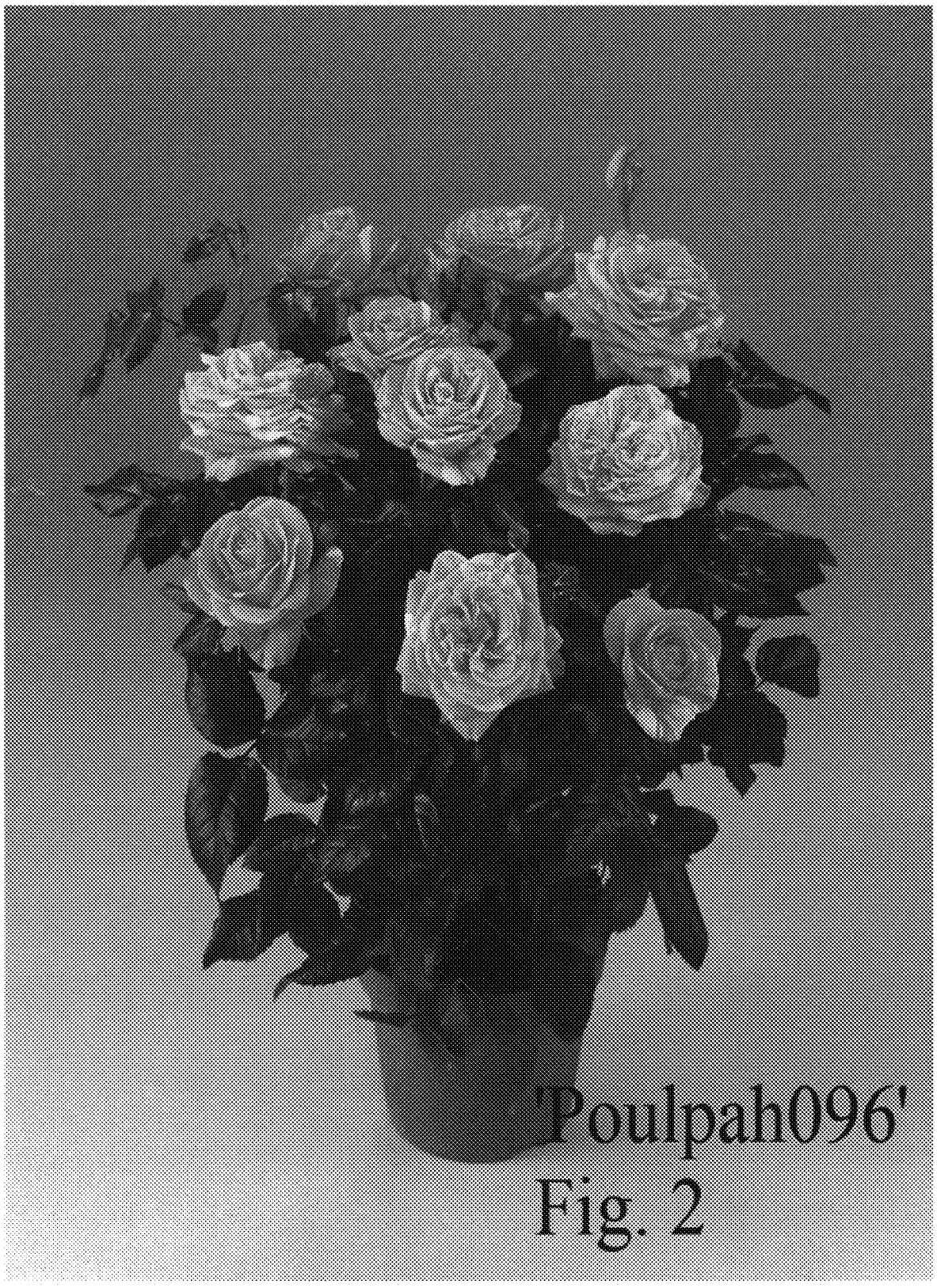

Specifically illustrated in FIG. 2 of the drawings is the new variety flowering in a container. Plants shown are 2 years of age.

DETAILED DESCRIPTION OF THE VARIETY

The following is a description of 'Poulpah096', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah068', U.S. Plant Pat. No. 25,970 are compared to 'Poulpah096' in Chart 1.

CHART 1

| | 'Poulpah096' | 'Poulpah068' |
|---|---|---|
| Petal Count | 45 petals | 20 petals |
| Flower Diameter | 50 to 70 mm | 75 mm |
| General Tonality of Flower Color | Red Group 38C | Red Group 52A with intonations of Red Group 43D. Splashed with White Group N155B |

Flower and Flower Bud

Blooming habit: Continuous.

Flower bud:

*Size*.—Upon opening, 25 mm in length from base of receptacle to end of bud. Bud diameter is 16 mm.

*Bud form*.—Ovoid.

*Sepal inner surface*.—Color: Yellow-Green Group 146D. Surface: Lightly pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—20 mm long, 9 mm wide.

*Receptacle*.—Texture: Smooth. Size: 7 mm in height, 9 mm wide. Color: Yellow-Green Group 144A with intonations of Greyed-Purple Group 183A. Shape: Funnel.

*Pedicel*.—Surface: Smooth. Length: 35 mm. Diameter: 2.5 mm on average. Color: Yellow-Green Group 144A with intonations of Greyed-Purple Group 183A. Strength: Strong.

*Peduncle*.—Length: 2 to 3 cm. Diameter: 3 mm. Color: Yellow-Green Group 144A. Texture: Smooth.

Flower bud development: Flower buds are borne singly or in clusters of up to three flower buds per stem.

Flower bloom:

*Fragrance*.—None.

*Duration*.—The blooms have a duration on the plant of approximately 15 days. Petals fall cleanly away from plant after flowers have fully matured.

*Size*.—Flower diameter is 50 to 70 mm when open. Flower depth is 23 to 28 mm.

*Flower shape*.—High centered, very double, with a high pointed center which is tightly closed.

*Shape of flower, side view*.—The upper portion is a flattened convex, and the lower portion is flat concave.

Petalage: Under normal conditions, flowers have about 45 petals.

General tonality of flower: Open flowers are Red Group 38C.

Petal color:

*Upon opening, outer petals*.—Upper surface: Red Group 37A with streaks of White Group 155 A, and occasionally Yellow Group 10D. Lower surface: Red Group 38A with streaks of White Group 155 A, and occasionally Yellow Group 10D.

*Upon opening, inner petals*.—Upper surface: Red Group 37A with streaks of Yellow Group 10D. Lower surface: Red Group 38A with streaks of Yellow Group 10D.

*Basal petal spots, upon opening*.—Upper surface: Medium sized Yellow Group 10A. Lower surface: Medium sized Yellow Group 10A.

*After opening, outer petals*.—Upper surface: Red Group 49A with streaks of White Group 155 A, and occasionally Yellow Group 10D. Lower surface: Red Group 49B with streaks of White Group 155 A, and occasionally Yellow Group 10D.

*After opening, inner petals*.—Upper surface: Red Group 49A with streaks of Yellow Group 10D. Lower surface: Red Group 49B with streaks of Yellow Group 10D.

*Basal petal spots, after opening*.—Upper surface: Medium sized Yellow Group 10A. Lower surface: Medium sized Yellow Group 10A.

Petals:

*Petal reflex*.—Slightly reflexed.

*Margin*.—Entire and uniform. Moderate undulations.

*Shape*.—Broad and elliptic. Apex shape: Rounded. Base shape: Acute.

*Size*.—21 mm (l)×22 mm (w).

*Texture*.—Smooth.

*Thickness*.—Average.

Reproductive flower parts:

*Pollen*.—None observed.

*Anthers*.—Size: 2 mm in length. Color: Yellow Orange Group 23C. Quantity: 45 on average.

*Filaments*.—Color: Yellow Group 13C. Length: 4 mm.

*Pistils*.—Length: 10 mm. Quantity: 28 on average.

*Stigmas*.—Color: Green-White Group 157A.

*Styles*.—Color: Green-White Group 157A.

*Location of stigmas*.—Superior in location relative to the length of the filaments and the height of the anthers.

*Hips*.—None Observed.

Plant

Plant growth: Upright and very compact. Plants are 20 to 25 cm in height, and 20 cm wide.

Stems:

*Color of juvenile growth*.—Yellow-Green Group 144B.

*Color of mature growth*.—Yellow-Green Group 144A.

*Length*.—Canes are about 11 cm from the base of the plant to the flowering portion.

*Diameter*.—About 5 mm.

*Internodes*.—On mature canes about 40 mm between nodes.

*Surface texture*.—Young wood: Smooth. Older wood: Smooth.

Long prickles: None observed.

Plant foliage:

*Compound leaf*.—140 mm (l)×110 (w).

*Quantity*.—2 leaves per 10 cm of stem on average.

*Leaf bearing angle to the stem*.—45 degrees.

*Color of juvenile foliage*.—Upper side: Yellow-Green Group 146A. Lower side: Yellow-Green Group 144A.

*Color of mature foliage*.—Upper side: Yellow-Green Group 146A. Lower side: Yellow-Green Group 146B.

Plant leaves and leaflets:

*Stipules*.—Size: 18 mm long, 2 mm wide. Quantity: 2 per compound leaf. Shape: Linear, slightly broad based with outward extending apices. Margins: Finely serrated. Color: Yellow-Green Group 144A.

*Petiole*.—Length: About 32 mm. Diameter: 2 mm. Texture: Smooth.

*Upper surface*.—Color: Yellow-Green Group 144A.

*Lower surface*.—Color: Yellow-Green Group 144A.

*Rachis*.—Length: About 50 mm. Texture: Smooth.

*Upper surface*.—Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 60 mm long, 45 mm wide. Shape: Generally elliptical. Base: Rounded. Apex: Acute. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* spp. Average resistance to black spot *Diplocarpon rosae*, and *Botrytis cinerea*.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah096', substantially as illustrated and described herein, due to its abundant pink and white striped flowers, disease resistance, and extended period of bloom.

* * * * *

'Poulpah096'

'Poulpah096'